US006160177A

United States Patent [19]

MacDiarmid et al.

[11] Patent Number: 6,160,177

[45] Date of Patent: Dec. 12, 2000

[54] OLIGOMERIC ANILINES AND THEIR SYNTHESIS

[75] Inventors: Alan G. MacDiarmid; Jing Feng; Wanjin Zhang, all of Drexel Hill, Pa.

[73] Assignee: The Trustees of the University of Pennsylvania, Philadeplhia, Pa.

[21] Appl. No.: 09/230,372

[22] PCT Filed: Jul. 25, 1997

[86] PCT No.: PCT/US97/13144

§ 371 Date: Dec. 6, 1999

§ 102(e) Date: Dec. 6, 1999

[87] PCT Pub. No.: WO98/04516

PCT Pub. Date: Feb. 5, 1998

Related U.S. Application Data

[60] Provisional application No. 60/022,694, Jul. 26, 1996.

[51] Int. Cl.[7] ..................... C07C 249/00

[52] U.S. Cl. ..................... 564/271; 564/434

[58] Field of Search ..................... 564/271, 434

[56] References Cited

PUBLICATIONS

Green et al., Aniline–black and allied compounds Part I, *J. Chem. Soc.*, vol. 97, (1910), pp. 2388–2403.

Green et al., Aniline–black and allied compounds Part II, *J. Chem. Soc.*, vol. 101, (1912), pp. 1117–1123.

Honzl et al., Polyaniline Compounds. II. The linear oligoaniline derivatives tri–, tetra–, and hexaanilinobezene and their conductive complexes, *J. Polymer Sci.*, No. 22, (1968), pp. 451–462.

Lu et al., Phenyl–capped octaaniline (COA): An excellent model for polyaniline, *J. Am. Chem. Soc.*, vol. 108, (1986), pp. 8311–8313.

MacDiarmid et al., Polyanilines: A novel class of conducting polymers, *Faraday Discuss. Chem. Soc.*, vol. 88, (1989), pp. 317–332.

Masters et al., Polyaniline: Allowed oxidations states, *Synthetic Metals*, vol. 41–43, (1991), pp. 715–718.

Wei et al., A one–step method to synthesize N,N'–BIS (4'–aminophenyl)–1,4–quinoenediimine and its derivatives, *Tetraedron Letters*, vol. 37, No. 6, (1996), pp. 731–734.

Wei et al., A study of the mechanism of aniline polymerization, *J. Polym. Sci. Pt. A.*, vol. 27, (1989), pp. 2385–2396.

Willstatter et al., *Ber.*, vol. 40, (1907), p. 2665–3689.

*Primary Examiner*—Samuel Barts
*Attorney, Agent, or Firm*—Woodcock Washburn Kurtz Mackiewicz & Norris LLP

[57] ABSTRACT

I

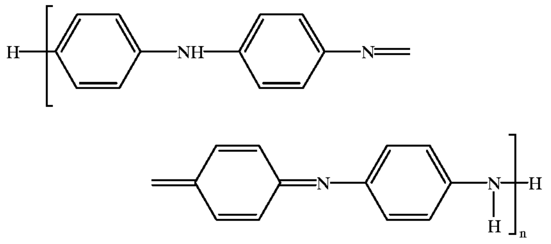

Oligomeric anilines (I; n=2, 4), useful in sensors for volatile organic compounds, in corrosion-resistant coatings for metals and metal alloys, and in applications which use electroactive materials, are prepared. Thus, tetraaniline in the emeraldine oxidation. state (n=1) was prepared by the ferric chloride-promoted oxidative coupling of N-phenyl-1,4-phenylenediamine HCl salt and recrystallizing the reaction mixture from PhMe, and next converted to tetraaniline in the leucoemeraldine oxidation state by treatment with hydrazine. Tetraaniline in the leucoemeraldine oxidation state was then contacted with an oxidative coupling agent (e.g., ammonium peroxydisulfate) to produce aniline oligomers I (n=2 and 4).

21 Claims, 7 Drawing Sheets

$C_{24}H_{20}N_4$ MW = 364
365
0
1300
MASS (MH+/e)

$C_{24}H_{22}N_4$ MW = 366
367
0
1300
MASS (MH+/e)

$C_{48}H_{38}N_8$ MW = 726
365
727
0
1800
MASS (MH+/e)

$C_{96}H_{74}N_{16}$ MW = 1450
365
727
1451
0
1800
MASS (MH+/e)

OLIGOMERIC ANILINES AND THEIR SYNTHESIS

RELATED APPLICATIONS

This application claims priority to U.S. Provisional Patent Application Serial No. 60/022,694, filed Jul. 26, 1996, the disclosure of which is hereby incorporated by reference herein in its entirety.

GOVERNMENT SUPPORT

Portions of the technology disclosed herein were supported principally by a grant from the Office of Naval Research No. N00014-92-J-1369 and, to a lesser extent, by NIST-ATP 1993-01-0149 subcontract from IBM.

FIELD OF THE INVENTION

This invention generally describes novel oligomeric anilines and novel methods of synthesizing oligomeric anilines.

BACKGROUND OF THE INVENTION

Polyaniline has been known for over 100 years and has been recently studied due to its properties as a conductive polymer after being doped with an appropriate species. Polyaniline is the name given to the polymer having the structure, in a completely reduced leucoemeraldine oxidation state, of the general formula:

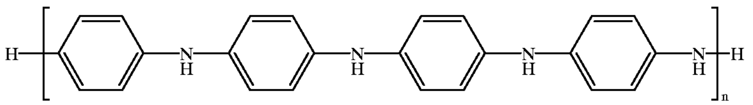

where n is greater than about 25. Oligomers of aniline, having the above structure where n is far less than 25, have attracted less attention in the scientific community.

Polyanilines can, in principle, exist in other oxidation states. Masters et al, *Syn. Met.,* 41–43, 715 (1991). For example, polyanilines can exist in the completely oxidized pernigraniline oxidation sate of the general formula:

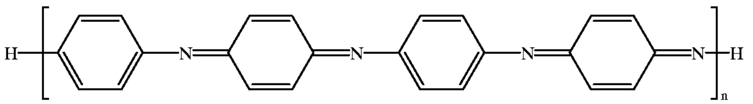

where n is about 25 or more.

Polyanilines can also exist in the partially oxidized emeraldine oxidation state of the general formula:

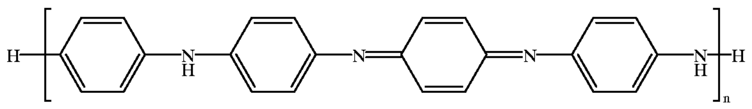

where n is about 25 or more.

The emeraldine oxidation state can be protonated by protonic acids, e.g., HA, to give polymers of the general formula:

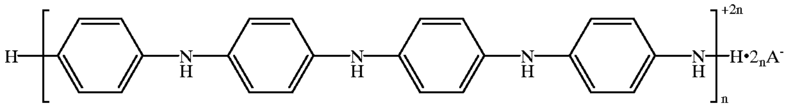

where n is about 25 or more, which exhibit a significant increase in electrical conductivity.

The synthesis of several oligomeric anilines including, for example, dianiline, N,N'-(4'-aminophenyl) phenylenediamine (e.g., trimer), N,N'-(4,4'-aminophenyl) phenylenediamine (e.g., amino-capped trimer), tetramer, phenyl-capped tetramer, phenyl-capped hexamer and phenyl-capped octamer, is described in the literature by U.S. Pat. No. 2,041,782, Willstatter et al, *Ber.,* 40, 2665 (1907); Honzl et al, *J. Polym. Sci.,* 22, 451 (1968); Liu et al, *J. Am. Chem. Soc.,* 108, 8311 (1986); Wei et al, *Tetrahedron Letters,* 37, 731 (1996); and Green and Woodhead, *J. Chem. Soc.,* 97, 2388 (1910).

The synthesis of some oligomers of aniline by the oxidative reaction of dianiline in an acidic aqueous solution is described by Willstatter et al, *Ber.,* 40, 2665 (1907). However, attempts to prepare higher oligomers through the oxidative coupling of a tetraaniline in the emeraldine oxidation state, as described by Wei et al, *J. Polym. Sci.* Pt. A., 27, 2385 (1989), have been unsuccessful.

It is now universally recognized, as described by MacDiarmid and Epstein, *Faraday Discuss Chem. Soc.,* 88, 317 (1989), that the so-called "octamer" of aniline allegedly produced by the oxidative polymerization of aniline, as described by Green and Woodhead, supra, and Green and Woodhead, *J Chem. Soc.,* 101, 1117 (1912), is actually a polymer of aniline having a molecular weight of about 325,000.

The present invention describes, among other things, novel oligomeric anilines and novel methods of synthesizing oligomeric anilines. The oligomeric anilines have utility as conductive materials in similar applications as polyanilines.

SUMMARY OF THE INVENTION

The present invention describes novel compounds of the formula (I):

(I)

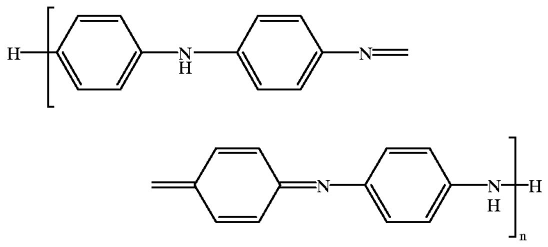

where n is 2 or 4.

The present invention describes novel methods of producing compounds of the formula (I), where n is 2 or 4. Tetraaniline in the emeraldine oxidation state is prepared and converted to tetraaniline in the leucoemeraldine oxidation state. The tetraaniline in the leucoemeraldine oxidation state is then contacted with an oxidative coupling agent to produce compounds of the formula (I) where n is 2 or 4.

These, as well as other, aspects of the present invention will become apparent from the following detailed description.

DETAILED DESCRIPTION OF THE INVENTION

Figure 1:
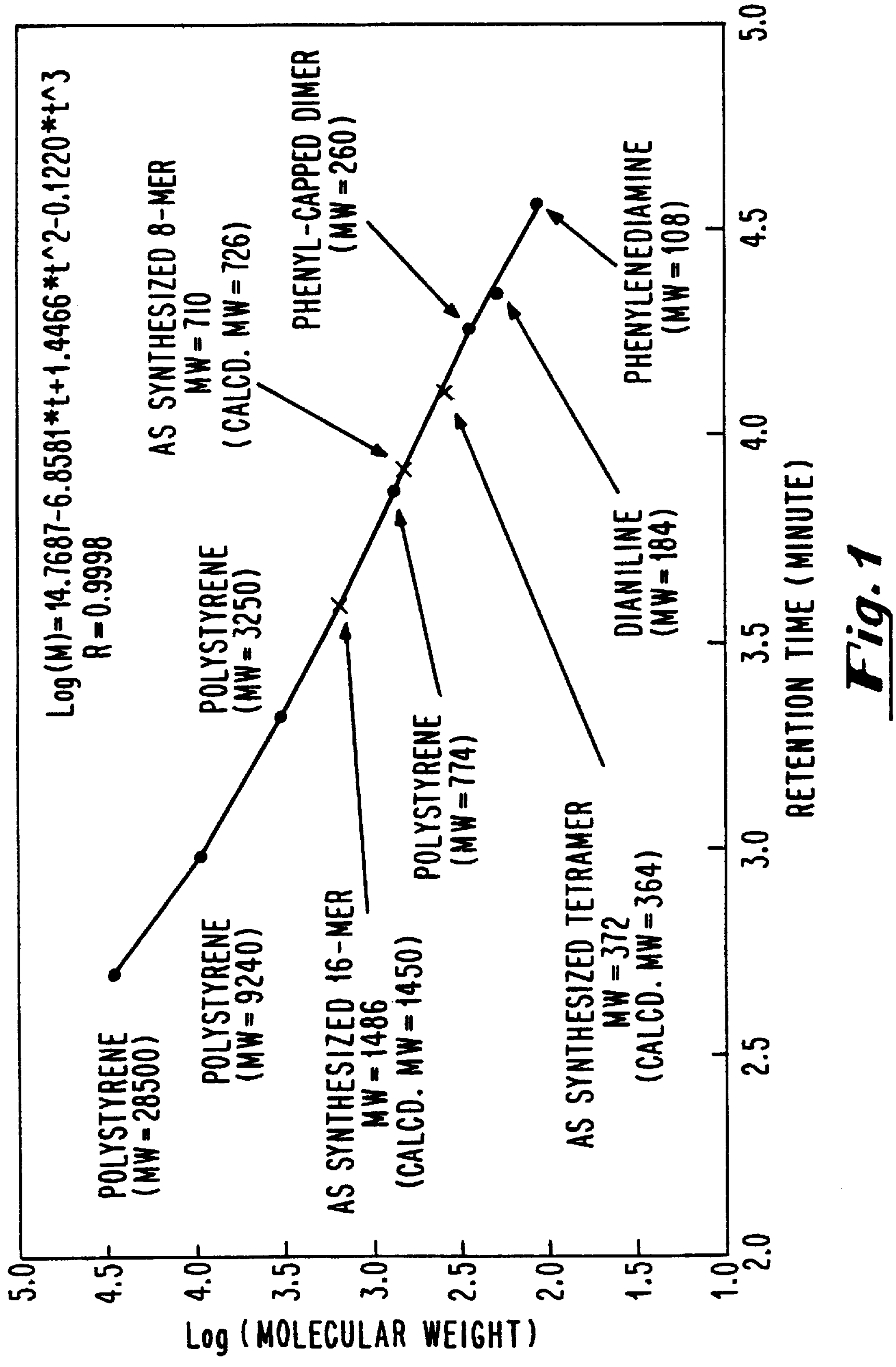
FIG. 1 is a graph of a gel permeation chromatography (GPC), taken in a tetrahydrofuran solvent, showing the molecular weights of known polystyrenes, phenyl-capped dimers, dianiline and phenylenediamine, as well as the experimentally determined molecular weights of tetraaniline (tetramer), a novel octaaniline (8-mer) and a novel hexadecaaniline (16-mer), all of which are in their emeraldine oxidation states, synthesized by the novel methods of the present invention.

As employed throughout the disclosure, the following terms, unless otherwise indicated, shall be understood to have the following meanings.

The term "tetraaniline" may also be referred to herein as "tetramer." The term "octaaniline" may also be referred to herein as "octamer" or "8-mer." The term "hexadecaaniline" may also be referred to herein as "16-mer."

The leucoemeraldine oxidation state of tetraaniline (where n=1), octaaniline (where n=2) and hexadecaaniline (where n=4) refers to a compound of the formula:

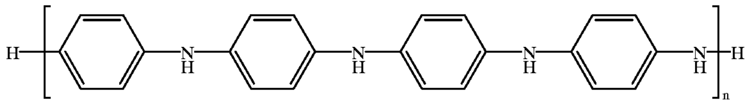

The emeraldine oxidation state of tetraaniline (where n=1), octaaniline (where n=2) and hexadecaaniline (where n=4) refers to a compound of the formula:

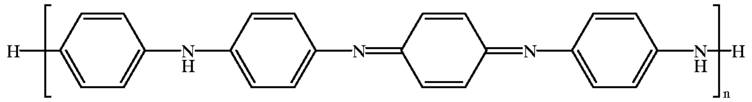

The pernigraniline oxidation state of tetraaniline (where n=1), octaaniline (where n=2) and hexadecaaniline (where n=4) refers to a compound of the formula:

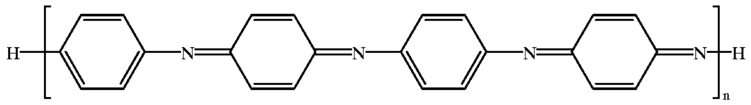

It has been unexpectedly discovered that the oxidative coupling of tetraaniline that is in a completely reduced oxidation state (e.g., the leucoemeraldine oxidation state), yields novel oligomeric anilines of the formula (I):

(I)

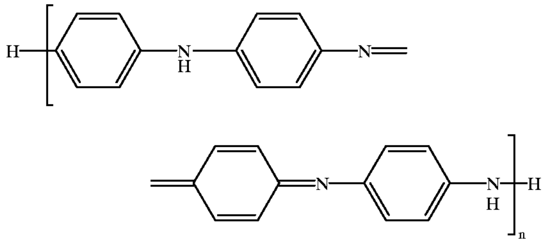

where n is 2 or 4. The octaaniline (n=2) or hexadecaaniline (n=4) is end-capped with a phenyl group at one end and an amine or imine at the other end.

In accordance with the present invention, there are described novel methods for synthesizing oligomeric anilines of the formula (I) wherein n is 2 or 4. Tetraaniline in the emeraldine oxidation state is prepared and converted to tetraaniline in the leucoemeraldine oxidation state. The tetraaniline in the leucoemeraldine oxidation state is then contacted with an oxidative coupling agent to produce compounds of the formula (I) where n is 2 or 4.

In general, tetraaniline in the emeraldine oxidation state can be prepared by methods that are well known to one skilled in the art, such as those described by, for example, Willstatter et al, *Ber.,* 40, 2665 (1907), the disclosure of which is hereby incorporated by reference herein in its entirety. A variation on the method described by Willstatter, supra, is as follows. An acidic aqueous solution of N-phenyl-1,4-phenylene-diamine hydrochloride salt (e.g., dianiline HCl in a concentration of about 0.01 M to about 0.5 M) may be quickly (e.g., within about 1 to about 2 seconds) combined with an acidic aqueous solution (e.g., about 0.1 M to about 1.0 M aqueous HCl, at a pH of about less than 2) of an oxidative coupling agent to produce tetraaniline in the emeraldine oxidation state. Suitable oxidative coupling agents include, for example, ferric chloride hexahydrate ($FeCl_3.6H_2O$), ammonium peroxydisulfate ($(NH_4)_2S_2O_8$), $Ce(SO_4)_2$, $KMnO_4$, $KBrO_3$, $K_2Cr_2O_7$, $KIO_3$, NaClO, and $H_2O_2$; most preferably ferric chloride hexahydrate or ammonium peroxydisulfate. In this reaction, the molar ratio of dianiline.HCl to the oxidative coupling agent is preferably from about 2:1 to about 1:2. Generally, the reaction is conducted at about room temperature (e.g., about 25° C.) for about 0.5 hours to about 4 hours.

In accordance with the synthesis methods of the present invention, the tetraaniline in the emeraldine oxidation state which is formed is then converted to tetraaniline in the leucoemeraldine oxidation state. In one embodiment, this is accomplished by contacting the tetraaniline in the emeraldine oxidation state with a reductant in a molar ratio of about 1:10 to about 1:20. Suitable reductants include, for example, anhydrous hydrazine, phenyl hydrazine, Pd/C (e.g., palladium on carbon catalyst) and $H_2$; preferably, the reductant is anhydrous hydrazine. The reaction may proceed in an appropriate solvent, such as an alcohol solvent, including, for example, methanol, ethanol or propanol. Preferably, the solvent is at a neutral pH and the concentration of the solution is from about 0.01 M to about 0.5 M. This reaction generally proceeds at an appropriate temperature, such as about room temperature (e.g., about 25° C.), for an appropriate amount of time, such as about 2 hours to about 12 hours.

Tetraaniline in the leucoemeraldine oxidation state is then contacted with an oxidative coupling agent to yield higher oligomers, including compounds of formula (I), wherein n is 2 or 4, as described herein. Suitable oxidative coupling agents for this reaction include, for example, ammonium peroxydisulfate, ferric chloride hexahydrate (iron (III) chloride), $Ce(SO_4)_2$, $KMnO_4$, $KBrO_3$, $K_2Cr_2O_7$, $KIO_3$, NaClO and $H_2O_2$, preferably ferric chloride hexahydrate or ammonium peroxydisulfate. In this reaction, the molar ratio of tetraaniline to oxidative coupling agent is preferably from about 3:1 to about 1:3, more preferably about 2:1 to about 1:2. Generally, the reaction is conducted at about room temperature (e.g., about 25° C.) for about 0.5 hours to about 4 hours. This reaction is generally conducted in an acidic aqueous solution (e.g., about 0.1 M to about 1.0 M HCl, at a pH of about less than 2).

Further to the above discussion, the product of the rapid oxidative coupling reaction of an oligomeric aniline in the leucoemeraldine oxidation state is determined by the molar ratio of the oligomeric aniline to oxidizing agent. Examples of such reactions are presented below. As will be apparent to one skilled in the art in view of the present disclosure, higher oligomeric anilines (e.g., where n is 8, 16 or 32 in formula (I)) can be synthesized by the appropriate choice of other molar ratios of reactant species and electrons (i.e., oxidizing agent). The molar quantity of electrons taken up by one mole of an oxidizing agent varies according to the oxidizing agent. For example, the equation $Fe^{+3}+e^{-}\rightarrow Fe^{+2}$ shows that one mole of electrons is taken up by one mole of an Fe(III) compound, e.g., $FeCl_3$. In another example, the equation $S_2O_8^{-2}+2e^{-}\rightarrow 2SO_4^{-2}$ shows that one mole of electrons is taken up by 0.5 mole of $S_2O_8^{-2}$ ion, as in $(NH_4)_2S_2O_8$. Based on the present disclosure, one skilled in the art could determine different ratios of oligomeric anilines (in the leucoemeraldine oxidation state) to various types of oxidizing agents.

(1) For the synthesis of tetraaniline in the leucoemeraldine oxidation state from dianiline, the molar ratio of dianiline:electrons is preferably about 1.0:1.0.

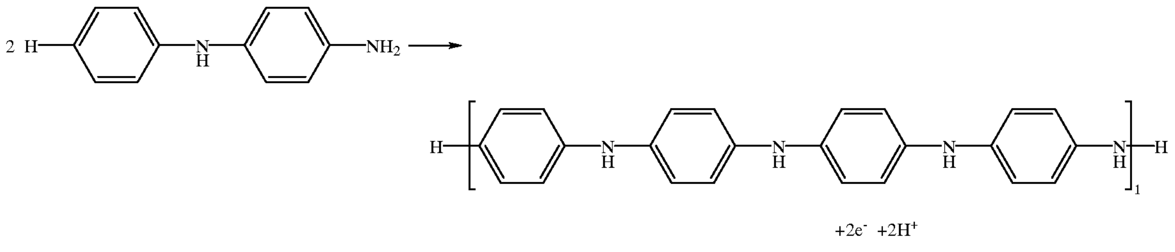

(2) For the synthesis of octaaniline in the leucoemeraldine oxidation state from dianiline, the molar ratio of dianiline-:electrons is preferably about 1.0:1.5.

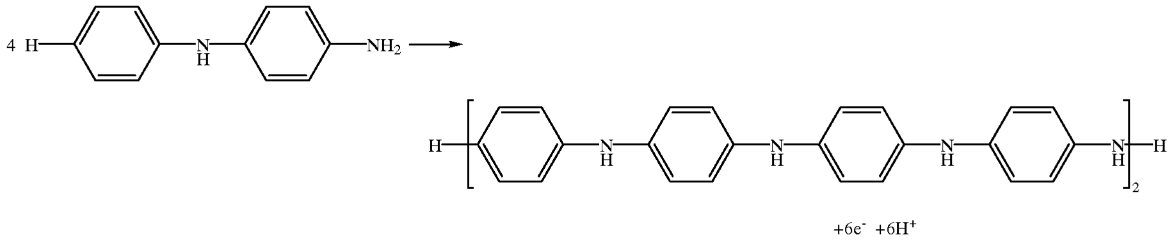

(3) For the synthesis of hexadecaaniline in the leucoemeraldine oxidation state from dianiline, the molar ratio of dianiline:electrons is preferably about 1.0:1.75.

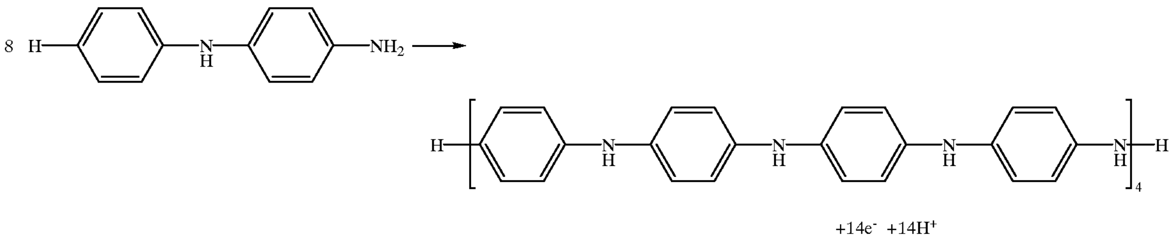

(4) For the synthesis of tetraaniline in the emeraldine oxidation state from dianiline, the molar ratio of dianiline-:electrons is preferably about 1.0:2.0.

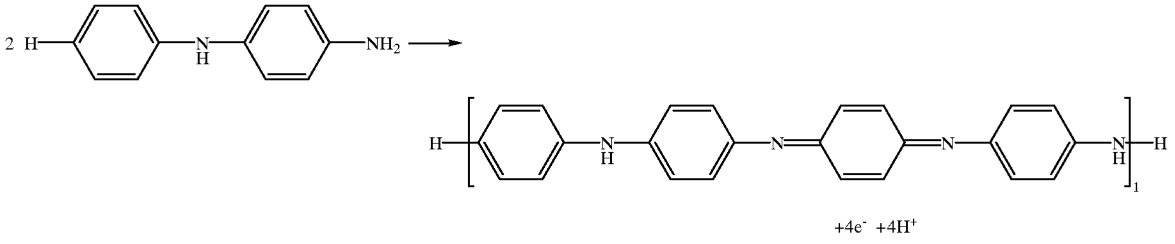

(5) For the synthesis of octaaniline in the emeraldine oxidation state from dianiline, the molar ratio of dianiline-:electrons is preferably about 1.0:2.5.

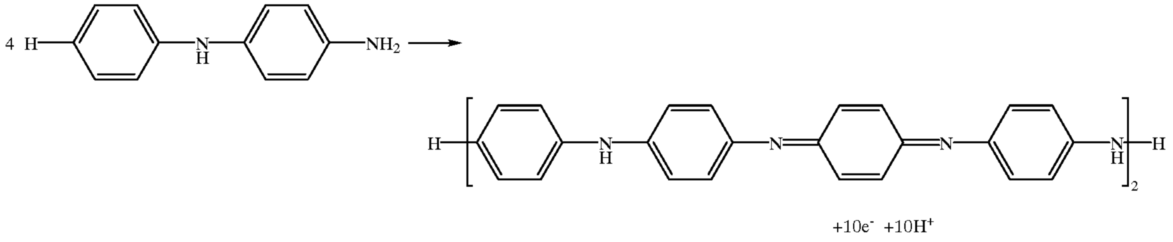

(6) For the synthesis of hexadecaaniline in the emeraldine oxidation state from dianiline, the molar ratio of dianiline:electrons is preferably about 1.0:2.75.

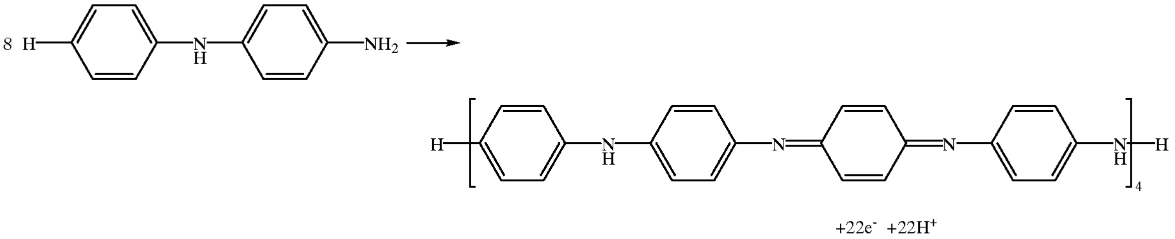

(7) For the synthesis of octaaniline in the leucoemeraldine oxidation state from tetraaniline, the molar ratio of tetraaniline:electrons is preferably about 1.0:1.0.

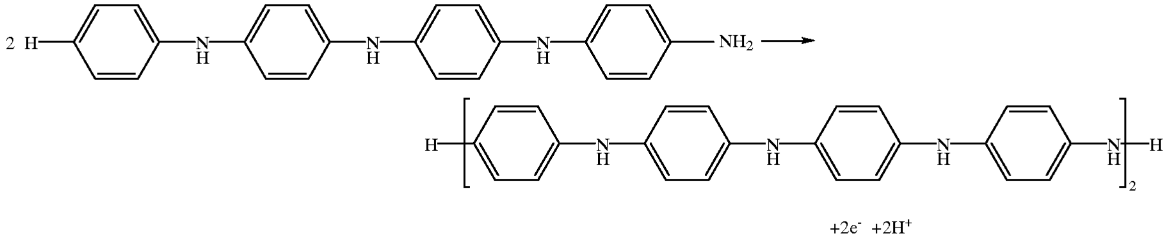

(8) For the synthesis of hexadecaaniline in the leucoemeraldine oxidation state from tetraaniline, the molar ratio of tetraaniline:electrons is preferably about 1.0:1.5.

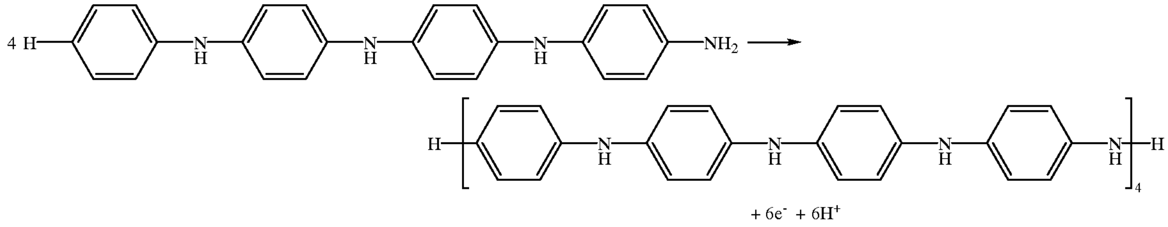

(9) For the synthesis of octaaniline in the emeraldine oxidation state from tetraaniline, the molar ratio of tetraaniline:electrons is preferably about 1.0:3.0.

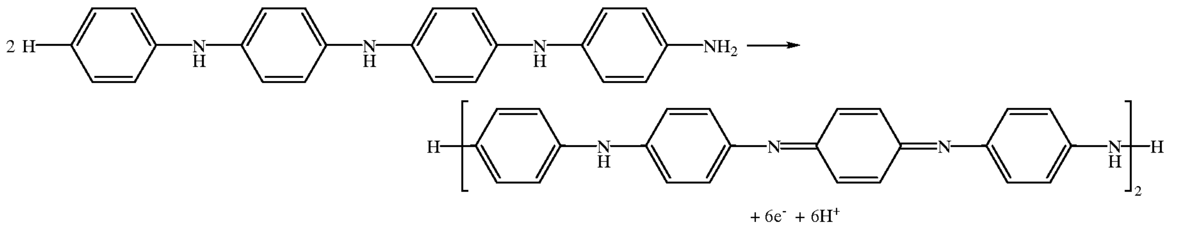

(10) For the synthesis of hexadecaaniline in the emeraldine oxidation state from tetraaniline, the molar ratio of tetraaniline:electrons is preferably about 1.0:3.5.

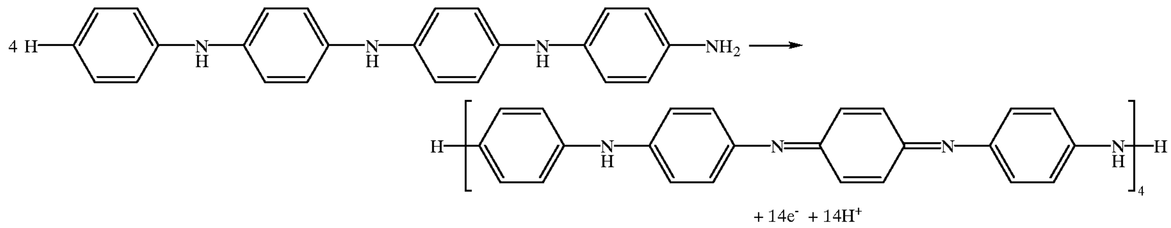

It can be seen from equations (1)–(10) above that the appropriate choice of molar ratio of a given oligomeric aniline in the leucoemeraldine oxidation state to oxidizing agent will favor formation of a higher oligomeric aniline in a preselected, desired oxidation state.

In the synthesis of octaaniline in the emeraldine oxidation state, some tetraaniline in the emeraldine oxidation state and hexadecaaniline in the emeraldine oxidation state are produced. Similarly, in the synthesis of hexadecaaniline in the emeraldine oxidation state, some tetraaniline in the emeraldine oxidation state and octaaniline in the emeraldine oxidation state are produced. A Soxhlet extraction and recrystallization process can be used to isolate the compound of formula (I) where n is 2 (octaaniline) or 4 (hexadecaaniline). Octaaniline in the emeraldine oxidation state may be extracted from a dried powder of the product described above by mixing it with a hydrocarbon solvent so that the octaaniline remains behind following a Soxhlet extraction process. Suitable hydrocarbon solvents include, for example, cyclohexane, toluene, hexane, benzene or a combination of petroleum ether and dimethoxymethane in a ratio of about 4:1 to about 1: 1, preferably cyclohexane. Hexadecaaniline in the emeraldine oxidation state may be extracted from a dried powder of the product described above by mixing it with an ether compound, such as diethyl ether, so that the hexadecaaniline remains behind following a Soxhlet extraction process. Other suitable hydrocarbon solvents and ether compounds that may be used for the extraction process can be readily determined by one skilled in the art in view of the present disclosure.

Figure 6:
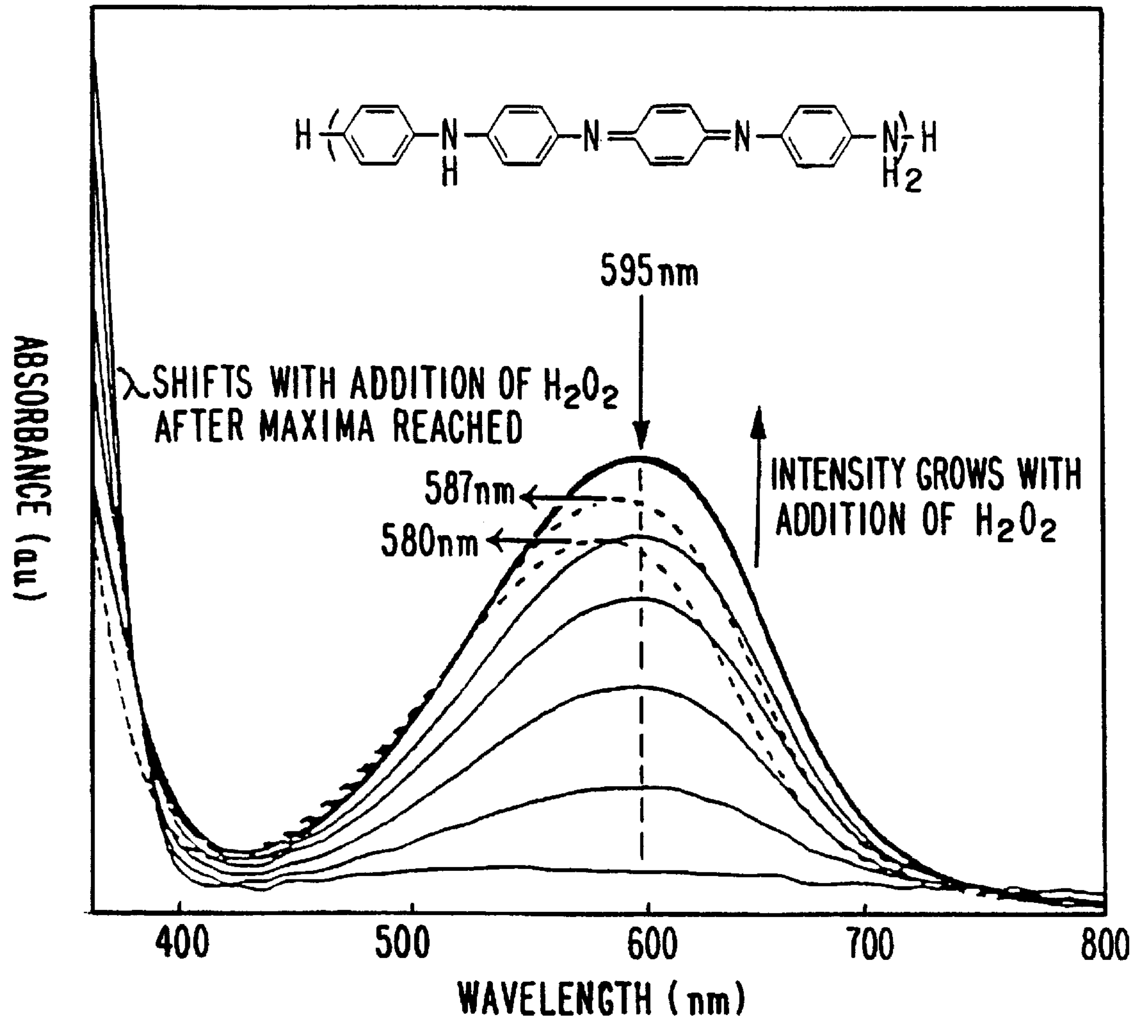
FIG. 6 is the UV/Vis spectra of the controlled step-wise oxidation of the leucoemeraldine oxidation state of octaaniline with $H_2O_2$ in N-methyl pyrrolidinone (NMP). The dotted spectra represent "over-oxidation." The 595 mn adsorption is the $\lambda_{max}$ of the emeraldine oxidation state of octaaniline.
Figure 7:
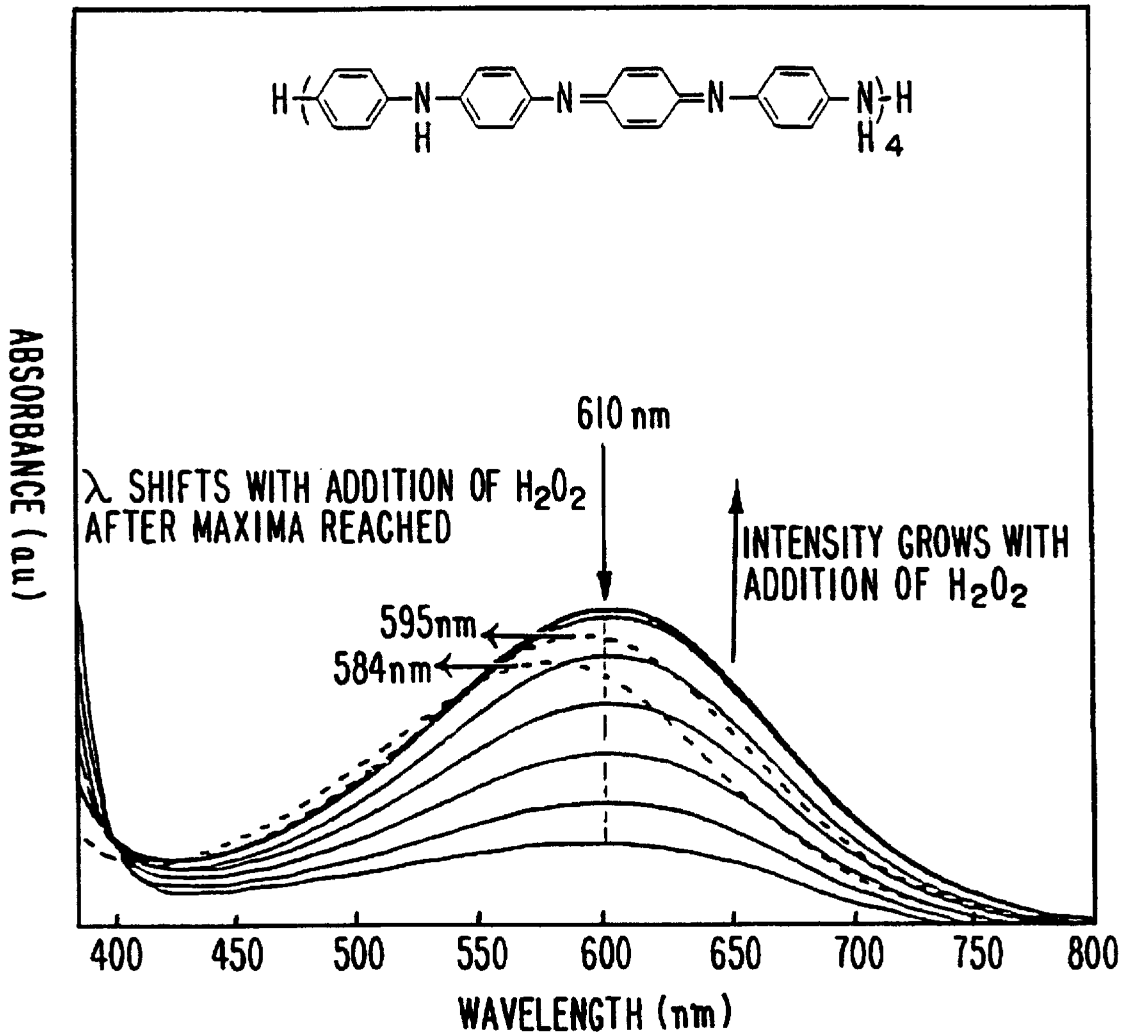
FIG. 7 is the UV/Vis spectra of the controlled step-wise oxidation of the leucoemeraldine oxidation state of hexadecaaniline with $H_2O_2$ in NMP. The dotted spectra represent "over-oxidation." The 610 nm adsorption is the $\lambda_{max}$ of the emeraldine oxidation state of hexadecaaniline.

A study of the octaaniline and hexadecaaniline produced by the process described above revealed that they were in the emeraldine oxidation state. To make this determination, each oligomer was first reduced by $N_2H_4$ to the leucoemeraldine oxidation state and was then controllably re-oxidized by the addition of $H_2O_2$, where its UV/Vis spectrum was constantly monitored (FIGS. 6 and 7). In each case, the "exciton" peak grew in intensity at its characteristic $\lambda_{max}$ until finally, on a further addition of $H_2O_2$, it started to undergo a blue shift. This revealed that the emeraldine oxidation state had been reached, and just exceeded, to form a more highly oxidized molecule. The $\lambda_{max}$ recorded just before the blue shift started is taken as representing the spectrum of the emeraldine oxidation state, as can be seen in comparing the $\lambda_{max}$ values given in FIG. 4.

The oligomeric anilines of the present invention are useful in preparing sensors for volatile organic compounds (VOC), for use in corrosion-resistant coatings for metals or metal alloys, and in other applications which use electroactive materials.

EXAMPLES

The following examples are presented for purposes of elucidation and not limitation. The examples are not intended, nor are they to be construed, as limiting the scope of the disclosure or claims.

Example 1

General Method of Synthesis and Purification of Oligomeric Anilines

A. Polymerization Method

An oxidant solution was made up by dissolving 0.05 mole ammonium peroxydisulfate (or 0.1 mole iron (III) chloride) in 150 ml distilled water at room temperature. A 0.1 mole portion of starting materials (hydrochloride salt of dianiline, hydrochloride salt of tetraaniline, etc.) was suspended in 500 ml of 0.6 M HCl with strong mechanical stirring at room temperature. The oxidant solution was poured into the suspension of the starting materials very quickly (within about 1~2 seconds) with strong mechanical stirring. As soon as the reactants were mixed, the suspension became a thick, dark blue paste. The mixture was then mechanically stirred for one hour at room temperature.

B. Purification by Filtering

The precipitate from section A was collected by filtering through a 110 mm diameter Buchner funnel, using a water aspirator with a #4 Whatman filter paper. The precipitate cake was placed in 500 ml of 0.1 M HCl. The resulting suspension was stirred for one hour, and filtered through the same Buchner funnel. This washing process was repeated five times.

C. Purification by Centrifugation

Alternatively, the precipitate from Section A was separated by centrifugation. The suspension was evenly distributed into three GS3 type plastic bottles (500 ml volume). The three bottles were then put into a GS3 type rotor evenly. The suspension was centrifuged, in a Sorvall superspeed centrifuge, at 9000 rpm rotation speed, for thirty minutes at room temperature. After the supernatant was decanted, 300 ml of 0.1 M HCl was added to each of the three bottles. The suspensions were magnetically stirred for one hour at room temperature and then centrifuged again by the same method. This process was repeated five times.

D. Dedoping

The purified precipitate from Section B or C was suspended in 600 ml of 0.1 M aqueous ammonium hydroxide solution and stirred for ten hours. The precipitate was collected on a 110 mm diameter Buchner funnel with #4 Whatman filter paper by a water aspirator. The precipitate was washed with distilled water six times and collected. It was transferred to a desiccator and pumped under dynamic vacuum for 48 hours at room temperature. The powder was further dried for 12 hours at 85° C. under dynamic vacuum to completely remove any trace of moisture before elemental analysis.

E. Synthesis of Oligoniers in the Leucoenieraldine Oxidation State

A 0.01 mole portion of oligomer (e.g., tetramer), synthesized from Section D, was suspended in 200 ml ethanol. Added into the suspension was 10 ml anhydrous hydrazine. The suspension was stirred for 12 hours at room temperature. Then, 100 ml distilled water was added, and the suspension was stirred for another hour. The precipitate was collected on a 60 mm Buchner funnel with #4 Whatman filter paper and washed three times with 200 ml distilled water. The gray powder was transferred to a desiccator and dried under dynamic vacuum for fifteen hours.

F. Gel Permeation Chromatography

Gel permeation chromatography (GPC) was developed for molecular weight characterization of higher polyaniline oligomers. The determination of molecular weight by GPC is in the error range of 5–10%. See, Kremmer et al, Gel Chromatography, p. 93, Wiley-Interscience publication, Hungary (1979).

Commercially available, narrow distribution polystyrene standards were used for establishment of a calibration curve. Due to the lack of low molecular weight polystyrene samples, some organic compounds with structures similar to the polyaniline oligomers were chosen for characterization of the low molecular weight part of the calibration curve. The standards were polystyrenes with molecular weights of 28500, 9240, 3250, and 774, respectively. The organic compounds were phenyl-capped dimer (MW=260), dimer (MW=184) and phenylenediamine (MW=108). The results are presented in FIG. 1.

Example 2

Synthesis of Tetraaniline

A. Materials

The following information applies to each of Examples 2–5: Chemicals were used as received, e.g., N-phenyl-1,4-phenylenediamine (98%), N-phenyl-1,4-phenylenediamine hydrochloride salt (98%), anhydrous hydrazine (98%), N-methyl-2-pyrrolidinone (NMP, 99%), phenylhydrazine (97%) (all from Aldrich Chemical Co.); and ammonium peroxydisulfate (98%), ferric chloride hexahydrate (99%), ammonium hydroxide (30%), sodium chloride (99%), hydrochloric acid (37%), active carbon (decolorizing DARCO G-60), diethyl ether (99%), ethanol (95%), hydrogen peroxide (30%), cyclohexane (99%), toluene (99%), tetrahydrofuran (THF 99%) (all from Fisher Scientific Co.).

The following information also applies to each of Examples 2–5: Vacuum filtration was carried out with a Buchner funnel (11.5 cm diameter) with #4 Whatman filter paper by using a water aspirator. Compounds were dried under dynamic vacuum for about 15 hours. Centrifugation was performed on a DuPont Sorvall superspeed centrifuge with a GS-3 type rotor and GS-3 type plastic containers at 9,000 rpm for 30 minutes at room temperature. Gel permeation chromatography (GPC) analyses were carried out on a Waters 510 HPLC equipped with 7 $\mu$m Ultrastyragel column (pore size 100 Å, effective molecular weight range about 50 to about 1,500) with THF as a solvent and a Waters 410 differential refractometer as detector. The column was calibrated by polystyrene standards and aromatic amines as described. NMR data were recorded at 500 MHz on an IBM Bruker NMR instrument and were listed in parts per million down field from tetramethylsilane (TMS). Elemental analyses (C, H, N) were performed on a Perkin Elmer 240C CHN elemental analyzer. Matrix-assisted laser desorption ionization mass spectroscopy was performed by Protein Chemistry Laboratory (University of Pennsylvania, Philadelphia, Pa.). UV/Vis spectra were recorded on a Perkin Elmer Lambda 9 photospectrometer. IR spectra were measured on a mixture of potassium bromide (FTIR grade, Aldrich) and sample by a Perkin Elmer FTIR 1760 instrument in diffuse reflectance mode.

B. Small Scale Synthesis of Tetraaniline

Ferric chloride hexahydrate 2.7 g (0.01 mole) was dissolved in 20 ml 0.1 M HCl at room temperature. N-phenyl-1,4-phenylenediamine hydrochloride salt 2.2 g (e.g., dianiline HCl, 0.01 mole) was dissolved in 250 ml 0.1 M HCl with stirring for 0.5 hours at room temperature. The solution was a clear green color. The ferric chloride solution was quickly (within about 1~2 seconds) added to the dianiline solution, with strong magnetic stirring. A dark blue precipitate immediately formed. Stirring was conducted throughout the reaction. The suspension was then stirred for 2 hours.

After 2 hours, the suspension was green in color. The reaction mixture was poured, with magnetic stirring, into a beaker containing 300 ml saturated sodium chloride solution. In order to promote agglomeration of the precipitate, the mixture was stirred for 0.5 hours and was kept in a refrigerator for 1 hour before vacuum filtration. The collected precipitate was transferred into 400 ml of distilled water. The suspension was stirred and the pH was adjusted to about 5~6 by adding 0.1 M $NH_4OH$ with constant stirring. The precipitate was collected by vacuum filtration, washed with 100 ml distilled water and transferred back into another 400 ml of distilled water. The pH of the solution was adjusted to about 7 by adding 0.1 M $NH_4OH$ in order to deprotonate the tetraaniline salt. The resulting suspension was stirred for 0.5 hours, and filtered through a Buchner funnel. The precipitate was washed with 1000 ml distilled water on the filter. The partly dried precipitate was held under vacuum for another 0.5 hours before it was dried.

The tetraaniline powder in the emeraldine oxidation state was obtained by recrystallizing 0.5 g of the precipitate from toluene (or, alternatively, $CCl_4$ or benzene) and was stored in a refrigerator. The yield was 0.25 g or 50%. A typical elemental analysis for tetraaniline $C_{24}H_{20}N_4$ was C: 78.81; H: 5.60; N 15.27; total: 99.68%. Calculated: C: 79.10; H: 5.53; N: 15.37. Mass spectrum (CI): 365 ($MH^+$/e). These data, as well as the (GPC spectrum, UV and FTIR are consistent with the proposed structure, and are presented in FIGS. 2–5, where it is identified as "A."

C. Large Scale Synthesis of Tetraaniline

N-phenyl-1,4-phenylenediamine hydrochloride salt was obtained by dissolving 18.4 g (0.1 mole) dianiline in 150 ml diethyl ether with constant stirring followed by the addition of 50 ml 6 M HCl. The precipitate was collected by vacuum filtration, washed with 50 ml diethyl ether and was then transferred to a 4000 ml beaker containing 2500 ml 0.1 M HCl with mechanical stirring, and was stirred for at least 0.5 hours at room temperature.

Ferric chloride hexahydrate 27.0 g (0.1 mole) was dissolved in 100 ml 0.1 M HCl at room temperature. The ferric chloride solution was quickly (within 1~2 seconds) added to the dianiline suspension, with strong mechanical stirring. A dark blue precipitate immediately formed. Vigorous stirring was continued for 2 hours.

The reaction mixture was then transferred into GS3-type plastic bottles for centrifugation and the supernatant was then decanted. 250 ml 0.1 M HCl was added to each bottle. The suspension was then stirred for at least 2 hours and the supernatant was decanted. This procedure was repeated at least three times. At the end of this washing procedure, the precipitate was transferred to a 4000 ml beaker with 1000 ml distilled water and was neutralized by adding 0.1 M $NH_4OH$ (until the pH was about 7 or about 800 ml). The precipitate was collected by vacuum filtration using a Buchner funnel (15.0 cm diameter) and was washed on the filter with 1500 ml distilled water and was then dried by a dynamic vacuum for more than 15 hours. This dried powder was used for the synthesis of the tetraaniline in the leucoemeraldine oxidation state.

Different molar ratios of dimer:oxidant, and different oxidants were also used in preparation of the tetraaniline. The results are presented in the table below.

TABLE 1

| Oxidant | Molar ratio (dimer:oxidant) | Crude product (g) |
|---|---|---|
| $(NH_4)_2S_2O_8$ | 2:1 | 9.0 |
| $(NH_4)_2S_2O_8$ | 1:1 | 10.5 |
| $FeCl_3.6H_2O$ | 1:1 | 9.0 |
| $FeCl_3.6H_2O$ | 1:2 | 11.1 |

Example 3

Synthesis of Tetraaniline in Leucoemeraldine Oxidation State

About 5.0 g of the tetraaniline in the emeraldine oxidation state synthesized in Example 2 was dissolved in 250 ml ethanol. 10 ml of anhydrous hydrazine was added with constant magnetic stirring. The reaction system was stirred for about 2 hours. The blue precipitate was collected by vacuum filtration and washed with 100 ml cold ethanol in 3 portions. The precipitate was suspended in 700 ml ethanol containing 1 ml of phenylhydrazine which was heated to reflux for 0.5 hours. The heat was removed and about 2.5 g of active carbon was added. The suspension was heated to reflux for another 0.5 hours and then was filtered hot by vacuum filtration and the filtrate was cooled in an ice bath. The off white precipitate was collected by vacuum filtration and washed with 50 ml cold ethanol and dried under dynamic vacuum. This precipitate was readily oxidized to, or approaching, the emeraldine oxidation state by air, especially if wet or in solution. Hence, minimum exposure to air is necessary in order to obtain the tetramer in the leucoemeraldine oxidation state. The dried precipitate was ground and stored in a dark bottle under Argon in a refrigerator. The yield was 3.5 g or 70%. A typical analysis for the tetraaniline in the leucoemeraldine oxidation state $C_{24}H_{22}N_4$ was C: 78.38; H: 6.02; N: 15.28, total 99.68%. Calculated, C: 78.68; H: 6.05; N: 15.29. Mass spectrum (CI): 367 ($MH^+$/e). $^1$H NMR (DMSO): 7.66 (s,1), 7.42 (s,1), 7.15 (s,1), 7.12 (t,2), 6.88 (m,12), 6.65 (t,1), 6.52 (d,2) and 4.63 (s,2). $^{13}$C NMR (DMSO): 145.7, 142.6, 139.9, 139.8. 135.1, 134.1, 133.5, 129.0, 121.0, 120.5, 119.6, 117.7, 116.3, 115.9, 114.9 and 114.4 (TMS std.). These data are in agreement with the proposed structure, and are presented in FIG. 3 where it is identified as "B."

Example 4

Synthesis of Octaaniline

Ferric chloride hexahydrate 5.4 g (0.02 mole) was dissolved in 20 ml 0.1 M HCl at room temperature. The tetraaniline in the leucoemeraldine oxidation state from Example 3 above 3.66 g (0.01 mole) was suspended in 250 ml 0.1 M HCl solution with magnetic stirring for 0.5 hours at room temperature. The ferric chloride solution was added very quickly (within 1~2 seconds) to the tetraaniline suspension with strong stirring. The suspension was then stirred magnetically for 2 hours. The reaction mixture was filtered, washed and neutralized following the general procedure described herein.

0.5 g of the dried powder was placed in a 25×100 cm Soxhlet thimble and was extracted with 300 ml cyclohexane for about 12 hours. The octaaniline powder remained in the thimble to yield 0.45 g or 90%. A typical elemental analysis for $C_{48}H_{38}N_8$ was C: 78.03; H: 5.72; N: 14.89, total 98.64%. Calculated, C: 79.32; H: 5.27; N: 15.42. Mass spectrum: 726 ($MH^+$/e). $^1$H NMR (DMSO): 8.36 (s,1), 6.96 (m,33) and 5.50 (s,2). $^{13}$C NMR (DMSO): 156.77, 154.70, 148.12, 148.02, 142.99, 142.85, 142.44, 141.50, 141.30, 139.15, 139.10, 139.05, 137.50, 136.30, 136.03, 134.80, 129.18, 129.01, 125.00, 124.52, 124.36, 123.93, 123.83, 123.73, 123.32, 123.10, 122.61, 119.94, 116.99, 116.89, 116.78 and 113.99 (TMS std.). These data are in agreement with the proposed structure.

Figure 2:
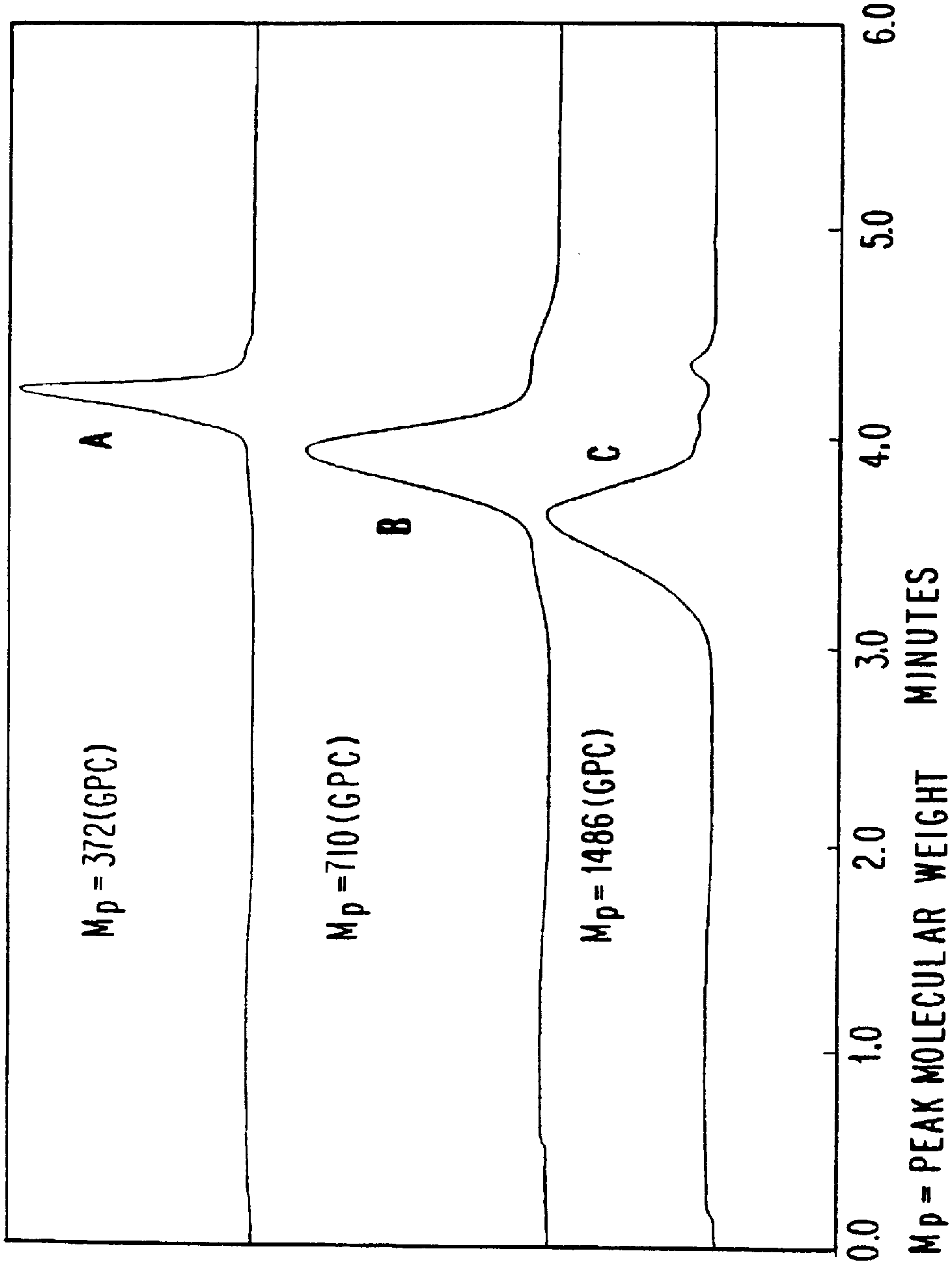
FIG. 2 is a graph showing the GPC profiles, taken in a tetrahydrofuran solvent, of tetraaniline in the emeraldine oxidation state (A); octaaniline in the emeraldine oxidation state (B), and hexadecaaniline in the emeraldine oxidation state (C).
Figures 3A, 3B, 3C, 3D:
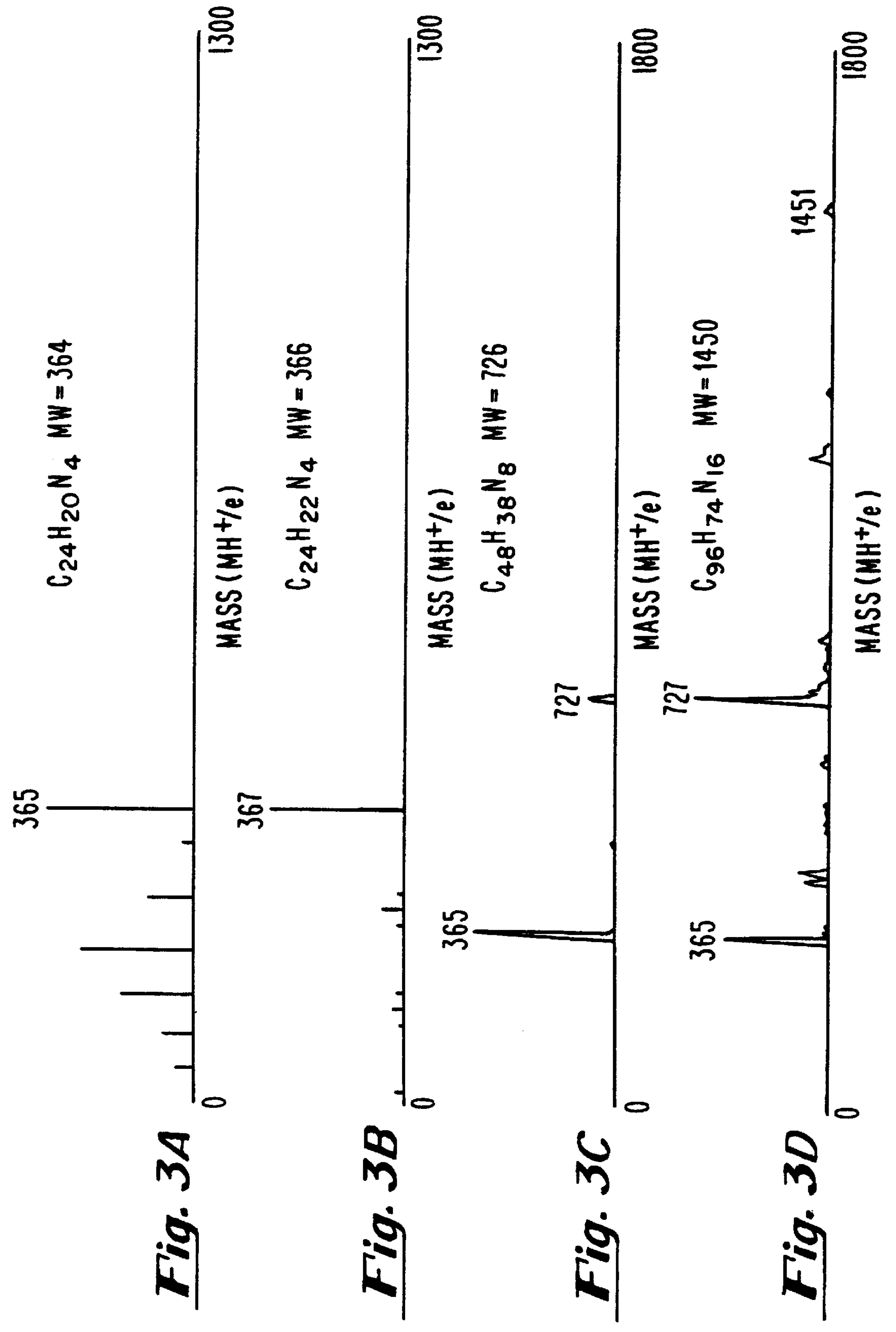
FIGS. 3A–D show the mass spectra of tetraaniline in the emeraldine oxidation state (FIG. 3A); tetraaniline in the leucoemeraldine oxidation state (FIG. 3B), octaaniline in the emeraldine oxidation state (FIG. 3C); and hexadecaaniline in the emeraldine oxidation state (FIG. 3D).
Figure 4:
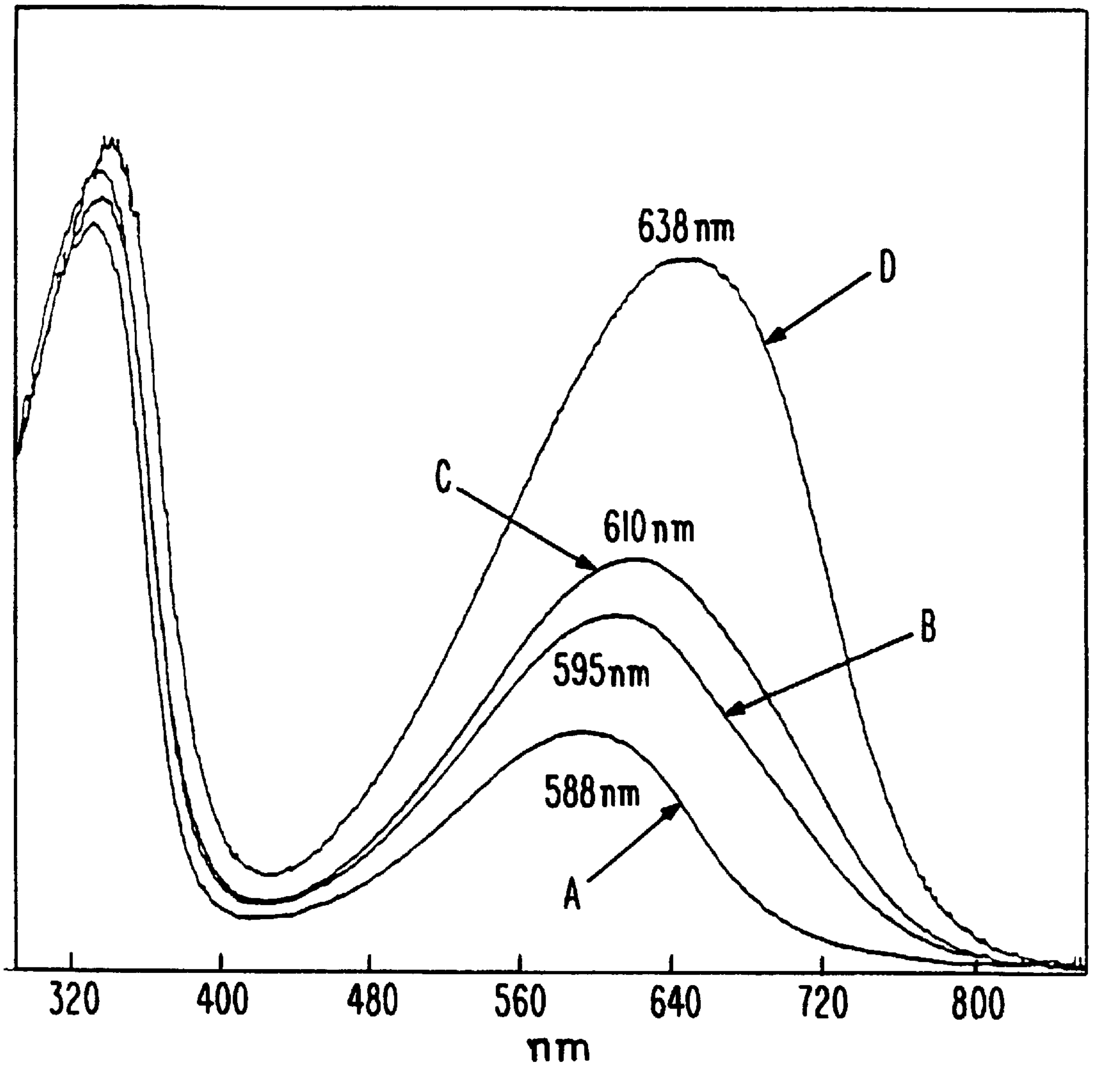
FIG. 4 is a graph showing the UV/Vis spectra, taken in a N-methyl pyrrolidinone (NMP) solvent, of tetraaniline in the emeraldine oxidation state (A); octaaniline in the emeraldine oxidation state (B); hexadecaaniline in the emeraldine oxidation state (C); and polyaniline emeraldine base (polyaniline EB) in the emeraldine oxidation state (D).
Figure 5:
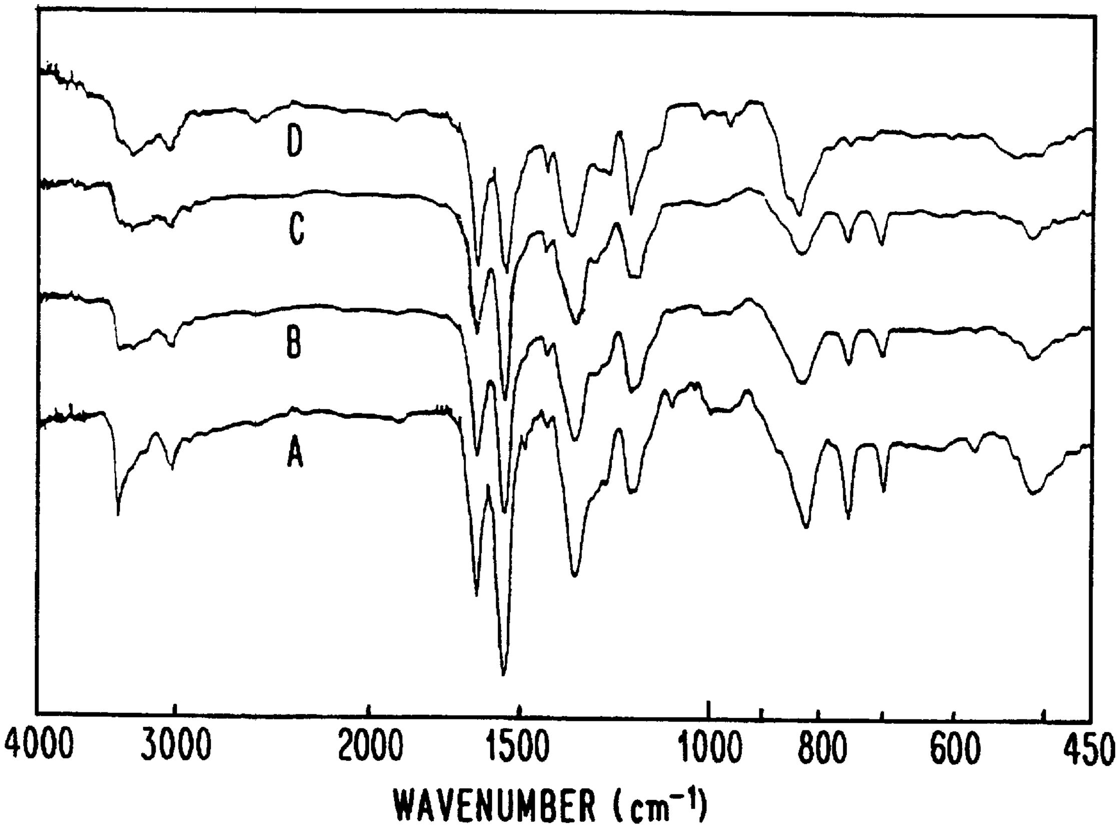
FIG. 5 is a graph showing the diffuse reflectance FTIR spectra of solid tetraaniline in the emeraldine oxidation state (A); solid octaaniline in the emeraldine oxidation state (B); solid hexadecaaniline in the emeraldine oxidation state (C); and solid polyaniline, "EB," in the emeraldine oxidation state (D).

The GPC, UV/Vis and FTIR spectra are presented in FIGS. 2, 4 and 5 where it is identified as "B." The mass spectrum is given in FIG. 3 where it is identified as "C."

Example 5

Synthesis of Hexadecaaniline

Ammonium peroxydisulfate 2.28 g (0.01 mole) was dissolved in 15 ml of 0.1 M HCl solution at room temperature. The tetraaniline in the leucoemeraldine oxidation state from Example 3 above 3.66 g (0.01 mole) was suspended in 250 ml 0.1 M HCl solution with magnetic stirring for 0.5 hours at room temperature. The ammonium peroxydisulfate solution was added very quickly (within about 1~2 seconds) to the tetraaniline suspension with vigorous stirring and was then stirred for an additional 2 hours, after which time it was filtered, washed and neutralized following the general procedures described herein. The dried powder was extracted with 300 ml diethyl ether using a Soxhlet extractor. The insoluble powder remaining in the thimble was the hexadecaaniline at a yield of 2.6 g or 70%. A typical elemental analysis for $C_{96}H_{74}N_{16}$ was C: 78.03; H: 5.10; N: 14.18, total 97.31%. Calculated, C: 79.43; H: 5.14; N: 15.44. Mass spectrum: 1451 ($MH^+$/e). $^1$H NMR (DMSO): 7.00 (broad). $^{13}$C NMR (DMSO): 129.11 (TMS std.). These data, as well as the GPC spectrum, UV and FTIR are consistent with the proposed structure, and are presented in FIGS. 2, 4 and 5 where it is identified as "C." The mass spectrum is given in FIG. 3 where it is identified as "D."

Example 6

Molecular Weight Characterization of Oligomeric Anilines

Tetraaniline, octaaniline and hexadecaaniline were dissolved in tetrahydrofuran (THF) before doing GPC experiments. The calculated molecular weights of tetraaniline, octaaniline and hexadecaaniline were 364, 726 and 1450, respectively. The molecular weights from the GPC calibration curve were 372 for tetraaniline, 710 for octaaniline and 1486 for hexadecaaniline, as shown in FIGS. 1 and 2.

Example 7

HCl Doping of Oligomeric Anilines 0.5 g of the above oligomeric anilines in their emeraldine oxidation state were suspended in 200 ml 1 M HCl with stirring for 24 hours at room temperature. The doped powder was collected by vacuum filtration and washed with 200 ml 1 M HCl. The powder was dried under dynamic vacuum. The conductivities of the HCl-doped oligomeric anilines in their emeraldine oxidation state were measured on compressed pellets using a 4-probe technique and are shown in the table below.

TABLE 2

| Compound | Conductivity (S/cm) |
|---|---|
| tetraaniline | $3.0 \times 10^{-3}$ |
| octaaniline | $1.7 \times 10^{-2}$ |
| hexadecaaniline | $4.0 \times 10^{-3}$ |
| polyaniline | 1.0~5.0 |

As can be seen from the table above, the conductivities of tetraaniline, octaaniline and hexadecaaniline are about 2 to 3 orders of magnitude lower than that of polyaniline, but at the same order of magnitude as that of alkyl-substituted polyanilines. Wei et al, *J. Phys. Chem.,* 93, 495 (1989).

The disclosure of each patent, patent application and publication cited in the present application is hereby incorporated by reference herein in its entirety.

Although the invention has been set forth in considerable detail, one skilled in the art will appreciate that numerous changes and modifications can be made to the preferred embodiments of the invention and that such changes and modifications may be made without departing from the spirit and scope of the invention.

What is claimed is:

1. A compound of the formula (I):

(I)

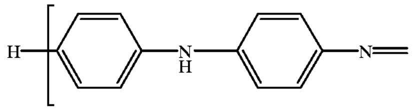

-continued

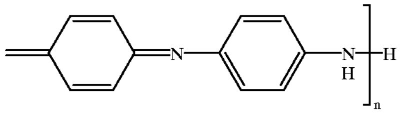

wherein n is 2 or 4.

2. The compound of claim 1, wherein n is 2.

3. The compound of claim 1, wherein n is 4.

4. A method of producing a compound of the formula:

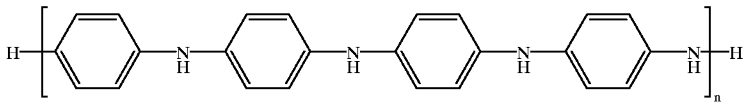

wherein n is 1, comprising:

preparing tetraaniline in the emeraldine oxidation state; and converting the tetraaniline in the emeraldine oxidation state to tetraaniline in a leucoemeraldine oxidation state.

5. The method of claim 4, comprising preparing the tetraaniline in the emeraldine oxidation state by reacting a salt of N-phenyl-1,4-phenylenediamine with an oxidative coupling agent; and dedoping the salt of the tetraaniline in the emeraldine oxidation state.

6. The method of claim 5, wherein the oxidative coupling agent is ammonium peroxydisulfate or ferric chloride hexahydrate.

7. The method of claim 4, comprising converting the tetraaniline in the emeraldine oxidation state to the tetraaniline in the leucoemeraldine oxidation state by contacting the tetraaniline in the emeraldine oxidation state with a reductant.

8. The method of claim 7, wherein the reductant is anhydrous hydrazine.

9. A method of producing a compound of the formula (I):

(I)

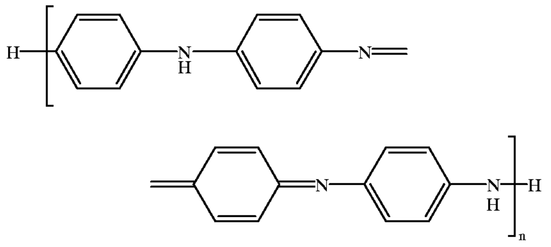

wherein n is 2 or 4, comprising:

preparing a tetraaniline in the emeraldine oxidation state;

converting the tetraaniline in the emeraldine oxidation state to a tetraaniline in a leucoemeraldine oxidation state;

contacting the tetraaniline in the leucoemeraldine oxidation state with an oxidative coupling agent to produce the compound of the formula (I).

10. The method of claim 9, wherein n is 2.

11. The method of claim 9, wherein n is 4.

12. The method of claim 9, comprising preparing the tetraaniline in the emeraldine oxidation state by reacting a salt of N-phenyl-1,4-phenylenediamine with an oxidative coupling agent; and dedoping the salt of the tetraaniline in the emeraldine oxidation state.

13. The method of claim 12, wherein the oxidative coupling agent is ammonium peroxydisulfate or ferric chloride hexahydrate.

14. The method of claim 9, comprising converting the tetraaniline in the emeraldine oxidation state to the tetraaniline in the leucoemeraldine oxidation state by contacting the tetraaniline in the emeraldine oxidation state with a reductant.

15. The method of claim 14, wherein the reductant is anhydrous hydrazine.

16. The method of claim 9, wherein the oxidative coupling agent is ammonium peroxydisulfate and ferric chloride hexahydrate.

17. The method of claim 9, wherein the method of producing the compound of the formula (I) is conducted in an aqueous solution.

18. The method of claim 9, further comprising extracting the compound of formula (I) with a hydrocarbon solvent to yield a compound of the formula (I) wherein n is 2.

19. The method of claim 18 wherein the hydrocarbon solvent is cyclohexane.

20. The method of claim 9, further comprising extracting the compound of formula (I) with an ether compound to yield a compound of the formula (I) wherein n is 4.

21. The method of claim 20 wherein the ether compound is diethyl ether.

* * * * *